(12) United States Patent
Elkind et al.

(10) Patent No.: US 6,862,398 B2
(45) Date of Patent: Mar. 1, 2005

(54) SYSTEM FOR DIRECTED MOLECULAR INTERACTION IN SURFACE PLASMON RESONANCE ANALYSIS

(75) Inventors: Jerome L. Elkind, Richardson, TX (US); Anita A. Strong, Richardson, TX (US); Andreas Hühmer, Mountain View, CA (US)

(73) Assignee: Texas Instruments Incorporated, Dallas, TX (US)

( * ) Notice: Subject to any disclaimer, the term of this patent is extended or adjusted under 35 U.S.C. 154(b) by 56 days.

(21) Appl. No.: 09/823,715

(22) Filed: Mar. 30, 2001

(65) Prior Publication Data

US 2002/0171841 A1 Nov. 21, 2002

(51) Int. Cl.[7] ........................ G01N 27/26; G01N 21/76
(52) U.S. Cl. ........................ 385/445; 385/73; 422/52
(58) Field of Search .................... 250/458.1, 459.2, 250/461.2, 436, 437, 440, 417; 422/52

(56) References Cited

U.S. PATENT DOCUMENTS

| | | | | |
|---|---|---|---|---|
| 5,327,225 A | * | 7/1994 | Bender et al. | 356/445 |
| 5,442,448 A | * | 8/1995 | Knoll | 356/445 |
| 5,485,277 A | * | 1/1996 | Foster | 356/445 |
| 5,779,976 A | * | 7/1998 | Leland et al. | 422/52 |
| 5,798,083 A | * | 8/1998 | Massey et al. | 422/52 |
| 5,846,485 A | * | 12/1998 | Leland et al. | 422/52 |
| 5,858,799 A | * | 1/1999 | Yee et al. | 436/164 |
| 5,935,779 A | * | 8/1999 | Massey et al. | 435/6 |
| 5,946,083 A | * | 8/1999 | Melendez et al. | 356/73 |
| 5,955,729 A | * | 9/1999 | Nelson et al. | 250/282 |
| 6,033,913 A | * | 3/2000 | Morozov et al. | 436/86 |
| 6,207,369 B1 | * | 3/2001 | Wohlstadter et al. | 435/6 |
| 6,325,973 B1 | * | 12/2001 | Leland et al. | 422/52 |
| 6,330,062 B1 | * | 12/2001 | Corn et al. | 356/445 |
| 2002/0168295 A1 | * | 11/2002 | Cunningham et al. | 422/82.05 |

* cited by examiner

*Primary Examiner*—John R. Lee
*Assistant Examiner*—David A. Vanore
(74) *Attorney, Agent, or Firm*—Wade James Brady, III; Frederick J. Telecky, Jr.

(57) ABSTRACT

Disclosed is apparatus and method for controlled surface plasmon resonance analysis having a surface plasmon resonance sensor (200) with a derivatized surface plasmon layer (116) in optical communication with the sensor, derivatizing the surface plasmon layer and placing an analyte detection chamber (102) in fluid communication with the derivatized surface plasmon layer. The chamber is adapted (118, 120) for the generation of a molecular interaction bias across the chamber. A conjugate is provided between an analyte and a bias responsive element, wherein the analyte is reactive with the derivatized surface plasmon layer and the bias responsive element changes the response of the analyte to the molecular interaction bias. A conjugated analyte may be introduced into the chamber, generating a molecular interaction.

13 Claims, 2 Drawing Sheets

SYSTEM FOR DIRECTED MOLECULAR INTERACTION IN SURFACE PLASMON RESONANCE ANALYSIS

FIELD OF THE INVENTION

The present invention relates in general to analytical sensor systems and, more particularly, to an apparatus and method for directing the interaction of molecules with a surface plasmon resonance (SPR) sensor.

BACKGROUND OF THE INVENTION

Without limiting the scope of the invention, its background is described in connection with analytical measurements and analyte detection of a wide variety of analytes using surface plasmon resonance (SPR) sensors.

SPR is an optical surface phenomenon that has been employed in sensors used in chemical, biochemical, biological and biomedical analysis. Summarized briefly, a surface plasmon is known in the art as a surface charge density wave at the surface of a thin conductive film. The oscillation of free electrons at a conductor-dielectric boundary is affected by the refractive index of the material adjacent to the film. Using a polarized beam of monochromatic light, surface plasmon polaritons can be excited. Resonance occurs when the polarized light is totally internally reflected from the conductive film. The light internally reflected from the film has a minimum intensity at the resonance angle. By detecting the resonance angle, the refractive index of a material adjacent to the film may be determined, which is indicative of other properties of the material. A more detailed description of surface plasmon resonance may be found in the article "Surface Plasma Oscillations and Their Applications," Rather, H., *Physics of Thin Films*, 1977.

With conventional sensors using surface plasmon resonance, a thin metal film is usually applied to a flat surface of a glass prism. A light source is tuned to direct incident light at the precise resonance angle. After passing through the prism and being reflected by the metal surface plasmon resonance layer, the light is directed by the prism to detectors. Determination of the resonance angle in conventional sensors having a separate light source, a prism and a detector requires a very high degree of precision in order to manufacture and align the separate optical parts so as to be able to produce accurate measurements. The usefulness of this approach, however, has been limited by system complexity related primarily to mechanical alignment issues.

Many problems associated with earlier sensors were overcome by the development of integrally formed SPR sensors in which some or all of the optical components are disposed inside a sensor housing transparent to radiation produced by the radiation source. In these sensors, the radiation source produces light that passes through the housing and strikes an exterior surface of the housing on which a thin conducting layer is formed. The light reflected from the conducting layer is directed toward an array of radiation detectors. The detector having the minimum output level is associated with radiation rays from the source that have bounced off the thin conducting layer at the "resonance" angle which is a function of the refractive index of the material contacting the conducting layer.

SUMMARY OF THE INVENTION

With conventional SPR sensors, when a substance is contained in a trace amount in the liquid sample analyzed, the sensitivity with which the substance to be analyzed is detected may be limited by the duration and volume of liquid in functional interaction with the sensor. In addition, to achieve the highest sensitivity in the assay, non-specific binding of interfering substances must be reduced. The present invention appreciates and comprehends these and other kinetic limitations on the use of SPR sensors.

Protein and oligonucleotide molecules are of particular interest in biosensing applications. The use of surface plasmon resonance in connection with biosensors obtained by virtue of derivatization of the surface plasmon resonance layer is known and described in, for instance, U.S. Pat. No. 4,889,427, which further describes introduction of sample to the derivatized layer by continuous-flow. Electrodes were provided to present changes in the dielectric constant of the medium and thus to prevent non-specific adsorption of test medium constituents.

Protein and oligonucleotide molecules may be directed or separated on the basis of their charge to opposite poles established in a dielectric environment. For example, oligonucleotides are negatively charged due to the presence of phosphate groups in the nucleic acid backbone. Under the influence of an applied electric field, oligonucleotides tend to migrate toward a positively charged surface. Controlled electric fields have been used to regulate the transport of single and double stranded oligonucleotides to selected locations for hybridization to immobilized substrates and for purposes of differential size separation. Amino acids may be both positively and negatively charged. The migration of proteins in an electric field depends on the distribution of diverse charges on the surface of the molecule.

The present invention provides ion capture assays, which involve a first specific binding molecule conjugated to a charged polymer. The ion capture complex is contacted to a solid phase material of opposite charge containing a second specific binding member. This type of assay has been used for separations in conventional chromatography and for analyte detection in test strip devices. Ion capture assay devices that employ a solid phase capture material typically require the use of, e.g., an indicator reagent. The complexes retained on a solid phase are detected via the label of the indicator reagent. Labels include fluorescent compounds, chromagens, chemiluminescent compounds, visual dyes, radioactive labels, enzymes and other substances capable of producing a detectable signal.

Furthermore, the rate at which analytes of interest bind to the solid phase in ion capture assays is typically limited by diffusion. A relatively long time may be required for substantially all of the potentially detectable components to diffuse and interact with the sensor surface. For large molecules and microbes, this waiting period may be especially prolonged. In many applications, particularly those involving sequential sets of test samples, a more rapid analysis would be desirable.

The present invention also provides a sensing device that increases the sensitivity of specific analytes by providing a motive force, particularly in conjunction with an integrally formed surface plasmon resonance sensor. A device that integrates the motive force and fluidic connectors and the various electro-optical sensing components on a single platform has widespread application. The present invention may be produced at a low-cost and allows for efficient, high-volume, mass production of sensors.

In one embodiment of the present invention, an ion capture type assay is employed for the real time detection of molecules as they bind to the solid phase. Since surface plasmon resonance measures a refractive index change that occurs as molecules bind to a sensing surface, no additional indicators, labels, or analysis techniques are required.

The rate at which analytes of interest bind to the solid phase in ion capture assays is typically limited by diffusion. In addition, to achieve the highest sensitivity in the assay, non-specific binding of interfering substances must be reduced. The electric field in one embodiment of the present invention directs the transport of charged molecules to selected locations, thereby concentrating them over an immobilized binding partner and consequently enhancing the rate of binding. Subsequent reversal of the field may be used to repulse nonspecific binding molecules whose affinity for the capture phase is less than that of the specific interaction. In combining a flow cell provided with positive and negative electrodes with an integrally formed SPR sensor, rapid sequential analysis of various analytes may be performed without alignment considerations. In one embodiment of the present invention, SPREETA™ sensors may be used for the detection of bio-molecular binding events through refractive index sensing. A capacitor may be created within the flow cell by creating a first electrode from the surface of the gold sensing layer and positioning a second electrode above the flow cell channel. The second electrode may be, e.g., platinum. The liquids and biological buffers typically used for most assays serve as the dielectric. If desired, the present invention may be adapted for use with gaseous test samples. Thus, the term "fluid" in the context of the present invention refers to both liquids and gases that flow on or about the sensor surface.

Without the aid of the present invention, a haptenated biofilm is applied to the gold sensing surface. The film contains specific chemical groups that bind (e.g., TNB groups). The kinetics of the antibody in solution binding to a target chemical group or analyte on the gold surface is both controlled by the affinity of the antibody and the diffusion kinetics.

In one embodiment of the present invention, the antibody may be conjugated to a large negatively charged polystyrene bead, having a field applied to bring it to the surface. Alternatively, the antibody may be conjugated to a large negatively charged polymer. Typical polymers include, for example, polyglutamic acid, polyaspartic acid, heparin and aliginic acids. One skilled in the art knows of several suitable reagents for labeling the primary amino groups of a protein with these molecules or other types of molecules of suitable size and charge. Once a negatively charged molecule is conjugated to the antibody, for example, the process of antibody binding is substantially accelerated by applying a positive voltage bias to the gold surface. Large negatively charged molecules are advantageous in this context because, by virtue of their size, a more profound change in refractive index is observed upon the interaction of larger molecules with the SPR sensing surface. Notwithstanding this advantage smaller molecules of either positive or negative charge may be used in conjugating various reactants.

In another embodiment, a magnetic field provides the motive force for transporting magnetically derivatized molecules to selected locations, concentrating them over an immobilized binding partner and consequently enhancing the rate of binding. Subsequent reversal of the magnetic field may be used to repulse nonspecific binding molecules whose affinity for the capture phase is less than that of the specific interaction. In the case of antibody molecules, for example, the antibodies may be conjugated to a magnetic bead or even a magnetically responsive element, e.g., iron. Several pre-activated magnetic beads that use standard cross-linking reagents are commercially available from companies such as Dynabead or Pierce Chemical Company.

The use of charged or magnetically derivatized reactants in SPR sensing assays allows the operator to control the binding kinetics. When used with an integrally formed SPR sensor, the resulting kinetically controlled integrally formed SPR sensor permits enhanced real-time detection using a device that is low-cost, efficient, high-volume, prealigned and calibrated, wafer-scale and that may be mass produced.

According to one embodiment of the invention, a flow cell is provided for directed molecular interaction in conjunction with analyte assays. The flow cell has in combination at least a fluid path having one or more fluidic conduits and connectors for entry and egress of analyte containing fluid, at least one analyte detection chamber disposed along the fluid path. At least one interior surface of the chamber is adapted for derivatization and a directed molecular interaction bias generator in fluid communication with the analyte detection chamber. A bias is generated across the chamber to direct a chosen analyte into a region proximate to the interior surface adapted for derivatization. Such a kinetically controllable flow cell would be useful in conjunction with a number of analytical systems.

In another embodiment, the interior surface adapted for derivatization of the flow cell is a surface plasmon resonance detection apparatus. In another embodiment, the interior surface adapted for derivatization of the flow cell is a surface plasmon resonance layer in optic communication with an integrally formed surface plasmon resonance sensor. The bias generated may be either electrical or magnetic. The flow cell may further contain, in fluid communication with the analyte detection chamber, a thermister for measuring the temperature within the cavity and, if desired, a heat regulating device to provide heating or heat exchange. The thermister and heat regulating devices may be interrelated and self regulating to desired conditions, which may be preset.

In one embodiment of the present invention a sample delivery and sensing unit is provided for directed molecular interaction during surface plasmon resonance analysis. The sample delivery and sensing unit has at least an integrally formed SPR sensor, a SPR layer in optic communication with the SPR sensor and in fluid communication with at least one kinetically controllable flow cell for modulating molecular interactions within an analyte detection chamber. In this embodiment, the SPR sensor has, at least, in fixed functional geometric alignment within, or affixed closely adjacent to, a housing transparent to a given frequency of light, at least one source of the light, at least one mirror and at least one photodetector array. The flow cell, adapted for attachment to the integrally formed surface plasmon resonance sensor, has at least one fluid path and an analyte detection chamber disposed along the fluid path having at least one interior surface in fluid communication with at least one surface plasmon resonance layer. The flow cell is adapted for generation of a molecular interaction bias across the chamber for supplying a motive force to bias responsive conjugated molecules. The generated bias permits controlled movement of the conjugated molecules to the surface plasmon resonance layer. The molecular interaction bias may be either electrical or magnetic. Correspondingly, charge bearing moieties are conjugated to the molecule to be biased in the case of an electrical bias generator. Magnetic moieties may be used or conjugated to the molecules to be biased in the case of a magnetic or electro magnetic bias generator.

Another embodiment of the present invention provides a sample delivery and sensing unit for directed molecular interaction during surface plasmon resonance analysis having at least one integrally formed SPR sensor, one thin SPR layer in optic communication with the SPR sensor and a directed molecular interaction flow cell. The integrally formed SPR sensor having, in combination and in fixed functional geometric alignment, a housing transparent to electromagnetic radiation in a given frequency range, a source of electromagnetic radiation having the given frequency range, at least one reflective surface and a photodetector array disposed within or closely adjacent the surface of the housing and substantially coplanar with the source. A thin SPR resonance layer is in optic communication with an exterior surface of the housing. The radiation source, SPR layer, reflective surface and photodetectors are disposed relative to each other so that the radiation from the source reflects off the reflective surface and strikes at least some of the photodetectors, whereby the radiation's intensity varies as a function of which photodetector is struck. The intensity variation function is affected by the index of refraction of a material that comes in contact with the outer surface.

The directed molecular interaction analysis flow cell has at least one analyte detection chamber in fluid communication with at least one surface plasmon resonance layer. The analyte detection chamber is adapted for generation of a molecular interaction bias across the analyte detection chamber to direct bias responsive conjugated molecules to the surface plasmon resonance layer. The molecular interaction bias across the analyte detection chamber may be, e.g., either electrical or magnetic.

The invention further provides a method and apparatus for kinetically controlled surface plasmon resonance analysis by the steps of, providing a surface plasmon resonance sensor having a surface plasmon layer in optical communication with the sensor, derivatizing the surface plasmon layer, an analyte detection chamber in fluid communication with the derivatized surface plasmon layer wherein the chamber is adapted for the generation of a molecular interaction bias across the chamber, and providing a conjugate between an analyte and a bias responsive moiety wherein the analyte is reactive with the derivatized surface plasmon layer and the bias responsive moiety changes the native response of the analyte to the molecular interaction bias. A conjugated analyte is introduced into the chamber, and a molecular interaction bias is generated. The changes in surface plasmon resonance due to association of the conjugated analyte to the derivatized surface plasmon layer is then determined. The generated molecular interaction bias may be, e.g., electrical or magnetic.

Further provided in one embodiment is a method for kinetically controlled surface plasmon resonance analysis wherein the conjugated analyte is adapted for the kinetically enhanced measurement of molecular interactions including avidin-biotin binding, antibody-antigen binding, antibody-antigen dissociation kinetics, protein binding, protein-nucleic acid interaction specific detection of small molecules, concentrations of analytes, measurement of oligonucleotide complements, mixture proportions, receptor-ligand interactions, aptamer interactions and molecular assembly events.

In one embodiment the method provides for kinetically controlled surface plasmon resonance analysis wherein the conjugated analyte is adapted for the kinetically enhanced measurement of molecular interactions in the serial measurements required by competitive binding assays.

BRIEF DESCRIPTION OF THE DRAWINGS

For a more complete understanding of the present invention, including its features and advantages, reference is made to the following detailed description, taken in conjunction with the accompanying drawings. Corresponding numerals and symbols in the different figures refer to corresponding parts unless otherwise indicated.

DETAILED DESCRIPTION

Figure 1:
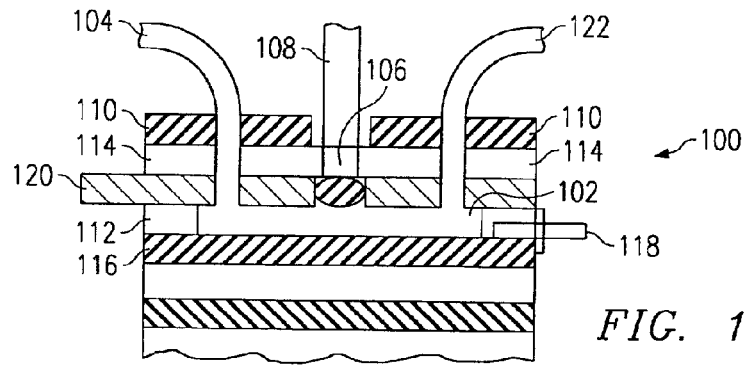
FIG. 1 illustrates a cross-sectional view of a temporally enhanced flow cell in accordance with the present invention.

While the making and using of various embodiments of the present invention are discussed in detail below, it should be appreciated that the present invention provides many applicable inventive concepts that may be embodied in a wide variety of specific contexts.

To facilitate the understanding of this invention, a number of terms are defined below. Terms defined herein have meanings as commonly understood by a person of ordinary skill in the areas relevant to the present invention. Terms such as "a", "an" and "the" are not intended to refer to one a singular entity, but include the general class of which a specific example may be used for illustration. The terminology herein is used to describe specific embodiments of the invention, but their usage does not limit the invention, except as outlined in the claims.

As used throughout the present specification, the following abbreviations are used:

| | |
|---|---|
| Au | gold |
| SMU | source measuring unit |
| SPR | surface plasmon resonance |
| SPREETA ™ | Texas Instruments' integrally formed SPR sensor |
| TNT | tri-nitrotoluene |
| TNB-BSA | tri-nitrobenzene bovine serum albumin |

The term "integrally formed SPR sensor" refers to a SPR sensor in which at least a portion of the detector system is disposed within a sensor housing that is transparent to radiation produced by a desired radiation source. Various radiation sources producing light detectable by photodetectors may be employed including for example light emitting diodes (LEDs), laser, incandescent lamp, filament or similar devices. Where the light source produces unpolarized light, a polarizer may be included after the light source to provide polarized light. Where the light source produces polarized light (as with certain lasers producing highly linearly polarized beams), polarizers may be eliminated. The light produced by the radiation source is able to pass through the housing and strikes an exterior surface of the housing on which a thin conducting layer is formed. Alternatively, the thin conducting layer may be disposed on a glass slide, or the like, which is located adjacent an exterior surface of the housing and having an index matching fluid disposed between the slide and the housing. In alternate embodiments, radiation sources and polarizers are also contained within the housing. Optionally, temperature sensors and other desired elements may be incorporated integrally or separately.

The term "E-field flow cell" refers to a flow cell constructed to permit the establishment of an electrically biased field within a detector portion of the flow cell. The electrically biased field is generated by opposite electrodes placed on, or in proximity to, a portion of a flow cell interior surface. At least one of the electrodes may also functions as, or is in functional proximately to, an analyte specific substrate such that generation of an electrical bias will concentrate charged molecules on or near the analyte specific derivatized plasmon layer.

The term "M-field flow cell" refers to a flow cell constructed to permit the establishment of a magnetic field within a detector portion of the flow cell. The magnetic field is generated by placement of at least one magnet or electromagnet on, or in proximity to, a portion of a flow cell interior surface. At least one surface able to serve as a magnet also functions as, or is in functional proximity to, an analyte specific substrate such that generation of magnetic field will concentrate charged molecules on or near the analyte specific derivatized SPR layer.

The following examples of possible embodiments are included for the sake of completeness of disclosure and to illustrate the methods and apparatus of the present invention. In no way are these examples intended to limit the scope or teaching of this disclosure. A description of the sensors employed herein may be found in, e.g., U.S. Pat. Nos. 5,946,083, 5,912,456 and 5,898,503, relevant portions thereof are incorporated herein by reference.

The advantages of the present invention are illustrated in FIGS. 1 through 5. FIG. 1 depicts a cross-sectional view of a portion of one embodiment of a flow cell 100 for regulating the interaction of molecules in accordance with the present invention. The flow cell 100 may be formed in one piece or may be formed of a sandwich of materials and may be composed of TEFLON fluorocarbon resin or other suitable inert material, including, for instance but without limitation, suitable metals, plastic and glass materials. The flow cell has at least one flow cell sample cavity 102 functioning as an analyte test or detection chamber. One or more surfaces of the flow cell sample cavity 102 may be derivativized and modified as suitable to form a sensor for measurement of a variety of molecules and interactions such as for example measurement of receptor-ligand interactions. The inflow conduit 104 functions as a channel through which one or more samples are guided into the flow cell sample cavity 102 and may be formed of suitable materials known in the art such as for instance those having the properties of plastic, nylon and/or metal tubing. Flow cell sample cavity 102 may include a probe for monitoring conditions within the cavity, for example, a bead thermister 106 connected via thermister contact 108 to distal monitoring equipment for monitoring the temperature of the flow cell sample cavity 102. In other embodiments, other conditions such as for example pH, pressure, etc. may be measured by providing one or more sensors (not shown) in fluid communication with the flow cell sample cavity 102.

In a sandwich-type construction such as the flow cell embodiment of FIG. 1, a metal or similar rigid housing plate 110 secures a gasket 112. Gasket 112 has at least one channel that forms a flow cell sample cavity 102. The gasket is placed between a TEFLON spacer 114 and an analyte reactive sensing surface 116. In this embodiment of FIG. 1, gasket 112 is composed of, e.g., silicone and the channel may be laser-cut. The analyte reactive sensing surface 116 is, e.g., a 50 nanometer thick gold ("Au") layer. Thermistor 106 may reside directly in the channel forming the flow cell sample cavity 102. In an embodiment of FIG. 1 where the flow cell is used in conjunction with an SPR sensor, the flow cell sample cavity 102 is positioned so that it overlays the active SPR region.

In accordance with the present invention, a capacitor for creating and controlling an electric field in a sample is created within flow cell sample cavity 102 by electrically coupling a first electrode connection 118 to the surface of the Au analyte reactive sensing surface 116. The first electrode connection 118 may comprise a thin strip of platinum placed in electrical contact with the gold surface and underneath the silicone gasket. By virtue of the electric coupling, the Au surface may serve as a first electrode. A second electrode 120 is located in a position substantially opposite to the Au analyte reactive sensing surface 116. The liquids and biological buffers used for most biosensing assays serve as the dielectric. The second electrode 120 may include a sheet of platinum placed between the silicone gasket and the Teflon block. As shown in FIG. 1, the first and second electrodes or connections thereto may protrude from the flow cell.

After measurement, the sample is evacuated from the flow cell sample cavity via outflow conduit 122. Flow cell 100 may include one or more liquid conduits directed appropriately for sampling to take place and one or more outlets that may be connected directly or though appropriate valving to a vacuum pump, e.g., contained within a host or ancillary unit (not shown). A liquid sample may therefore be pulled into analyte detection chamber 102 of the flow cell 100 and guided across an analyte reactive sensing surface 116. The analyte reactive sensing surface is most typically a derivatized surface plasmon layer in optic communication with an integrally formed surface plasmon resonance sensor.

The surface plasmon layer may be derivatized in a number of ways for binding selective ligands to a metal layer. The derivatization process may be a single step or several step process in which a first organic layer is deposited followed by binding (e.g., covalently) of selected ligands depending on the desired analyte to be detected.

After measurement, rather than proceeding into the pump, the test sample is caught in one or more waste receptacles outside of the flow cell (not shown). Other sensing system configurations according to the present invention may use one or more valves for dynamic sampling, including applying one or more reagents contained in one or more reservoirs. One or more reservoirs may also contain cleaning solutions or materials for calibration purposes.

A sample delivery and sensing unit may additionally include a thermal heat generating device, such as a heating coil. The sample delivery and sensing unit may further include a thermal heat exchange device, such as fan, for example. Thermal heat generating and/or thermal heat exchange devices may function to stabilize the temperature within the flow cell or between the flow cell and the surface plasmon sensor.

In one embodiment, the electrodes are connected to a source measuring unit (SMU) such as for example a Keithley model 236 source measuring unit (SMU). The SMU is used to source voltage and measure current during the course of the assay.

In a conventional direct binding SPR assay, an analyte is typically bound to an immobilized ligand on the SPR surface. The changes in local refractive index that occur during analyte binding describe the kinetics of interaction between the two molecules. For example, an antigen to which an antibody has been raised is attached to the surface of the SPR sensor. A dilute solution of specific antibody, for example, a monoclonal antibody or fragment thereof, is allowed to flow across the sensor surface. Binding of the antibody results in a change in refractive index. Similarly, the characteristics of other receptor ligand interactions may be evaluated in this way to determine binding kinetics.

Ligand concentration can be measured by SPR. One such ligand concentration measurement is performed using a competitive binding assay. In the case of an antigen-antibody competitive binding assay, the antibody is used as a large mass molecule whose binding is competitively prevented by free antigen or ligand in solution. When the antibody binds to the ligand bound to the gold SPR surface a linear increase in refractive index is observed. Samples of antibody containing ligand show a change in the rate of antibody adsorption and in the amount of antibody bound.

In accordance with a feature of the present invention, the antibody may be conjugated to a negatively charged polystyrene bead. The bead serves to amplify the changes in refractive index that occur upon binding of the antibody to the sensor surface as a result of its large mass. In addition, negatively charged sulfate groups on the polystyrene bead may increase the rate at which the antibody binds to the ligand on the sensor surface when a positive bias is applied to the surface. Antibody binding is typically limited by diffusion. The electric field in the E-field assisted assay helps to transport and concentrate the antibody over its immobilized binding partner to enhance the rate of binding.

In one embodiment of a competitive binding assay, the sensor is first calibrated by introducing into the flow cell analyte detection chamber a volume of anti-ligand antibody conjugated to beads, for example, 0.5 micron polystyrene beads, in a surfactant containing buffer that reduces non-specific interactions (e.g., 50 mM glycine+0.1% Triton X-100). A positive bias is applied to the Au surface containing the immobilized ligand to which the antibody is directed. A typical electrical bias may be, e.g., a 1–10 volt pulse for 1–10 seconds. The electric field is subsequently reversed to repulse the non-specific binding of molecules whose affinity for the ligand is reduced. A typical reversal bias may be, e.g., a 1–10 volt pulse for 1–10 seconds. A baseline is again obtained in 50 mM glycine+0.1% Triton X-100. Binding of anti-ligand antibody to the sensor surface is seen as a refractive index increase. The peak height for this "reference sample" ([ligand]=0) describes the maximum amount of anti-ligand antibody expected to bind without interference. A reference may be evaluated periodically to verify that the regeneration process does not affect the ability of the ligand derivatized surface to bind anti-ligand antibody.

The antibody may be stripped from the sensor and the surface regenerated using, e.g., 0.1% Triton+0.12 N NaOH. Antibody binding may be examined in the presence of a liquid sample containing, e.g., 0 or 1 ppm of the ligand. The presence of ligand in the liquid sample reduces the amount of antibody binding to the sensor surface. Samples are considered positive for ligand when the amount of antibody binding in the presence of the liquid sample is demonstrably and reproducibly less that obtained when antibody is bound in the buffer above (e.g., 50 mM glycine+0.1% Triton X-100 alone).

In one embodiment of the present invention, the flow cell is disposed such that the flow cell sample cavity 102 of FIG. 1 is in fluidic contact with the sensing surface of an integrally formed surface plasmon resonance sensor. One embodiment of such an integrally formed surface plasmon resonance sensor 200 is depicted in FIG. 2.

Figure 2:
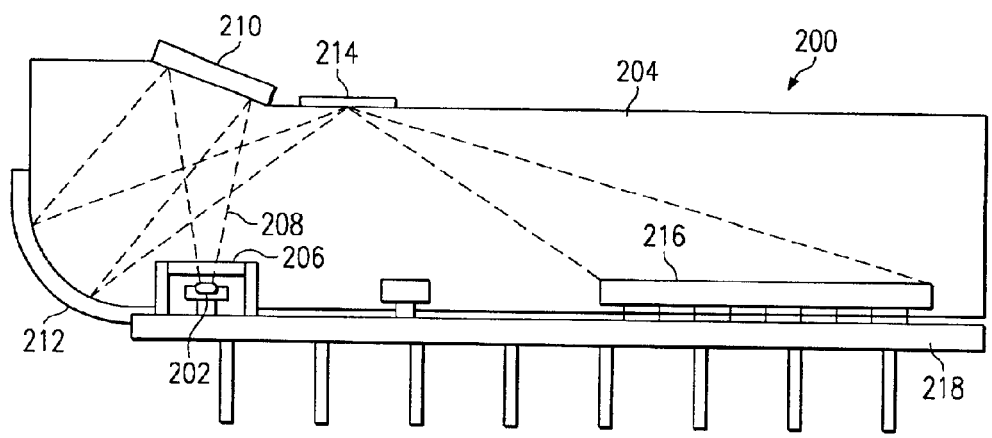
FIG. 2 illustrates one embodiment of an integrally formed surface plasmon resonance sensor.

In the integrally formed surface plasmon resonance sensor 200 of FIG. 2, a light source 202 (e.g., a light emitting diode (LED), a laser diode or any other suitable source of radiation), is disposed within a housing 204. The housing 204 is made of a material that is transparent to the radiation from the source 202 (e.g., suitable plastics or epoxy). A number of materials have been found suitable for construction of integrally formed sensor housings. In particular, an epoxy marketed under the trademark EPOCAST 2013 Parts A/B by Furane Products Company has been found useful especially for radiation sources in the infrared range. Other usable materials include, e.g., Emerson & Cumming, STYCAST 1269A Parts A/B, Tracon TRABOND F114, Dexter HYSOL OS1000, Norland 61 and 63, Dexter HYSOL MG18 or Nitto 8510-1100.

A polarizing filter 206 is disposed in a position after the radiation source 202 to produce polarized light 208. There are many suitable polarizers such as the plastic polarizing material (e.g., a Polaroid HN7 Linear Polarizer). Because light source 202 acts like a point source of light, the light rays diverge from each other. Likewise, the polarized light 208 has rays that are diverging from each other.

The diverging polarized radiation reflects from a planar mirror 210 that is disposed so that the plane thereof is not normal to the direction to the polarized radiation 208. The diverging polarized radiation, after being reflected from the mirror 210, is directed toward a curved (concave) mirror 212 disposed on a curved exterior surface of the housing 204. When the mirror 212 is concave, the shape of this mirror may be constructed so that the radiation reflecting therefrom converges at SPR layer 214.

The surface plasmon resonance layer 214 includes a thin layer of a conductive material such as, for example, copper, silver, gold or other suitable materials exhibiting surface plasmon resonance. The layer 214 is generally planar although other configurations, such as convex or concave configurations, or featured with steps, periodic or non-periodic, may also be used. This layer 214, in one embodiment of the invention, may include a film of gold approximately 500 angstroms thick. The thickness of a surface plasmon resonance layer may vary from about 200 to about 600 angstroms (20 to about 60 nanometers) and still permit surface plasmon resonance to occur. The specific film thickness is determined by experimentation with respect to the frequency of the radiation for the source 202 and the properties of the conductive material used for layer 214. When radiation strikes a thin conductive film at the interface of an insulator, the intensity of reflection therefrom is a function of the angle of incidence of the radiation onto the film and the refractive index of the material in contact with the other side of the film. Hence, by determining the angle at which minimum reflectance occurs, it is possible to determine the index of refraction of the material on the side of the film opposite the side the radiation is reflected from.

The configuration depicted in FIG. 2 produces diverging radiation that is reflected from the thin surface plasmon resonance layer 214. The diverging radiation passes through the housing 204 and is intercepted by a detector array 216 disposed at or near an external surface of the housing 204. The housing 204 is disposed upon a lead frame 218, which is in electrical connection with the light source 202 and the detector array 216. In addition, any desired ancillary integral equipment such as for instance, reference light sources and/or temperature sensors would be placed in electrical communication with the lead frame 218. For optical radiation, the detector array 216 may include an array of photodetectors. Each detector in the array 216 produces a signal on an output pin with a voltage that is proportional to the intensity of the radiation striking the detector. By measuring the voltage at each detector and knowing the angle that the radiation striking that detector intercepted the surface plasmon resonance layer, a plot of reflected radiation intensity as a function of the angle is produced. That plot generally correlates to the index of refraction of the substance on the side of the surface plasmon resonance layer opposite the side that reflects the radiation. The physical location of the elements illustrated in FIG. 2 may be moved or relocated while retaining the function described above.

Figure 3:
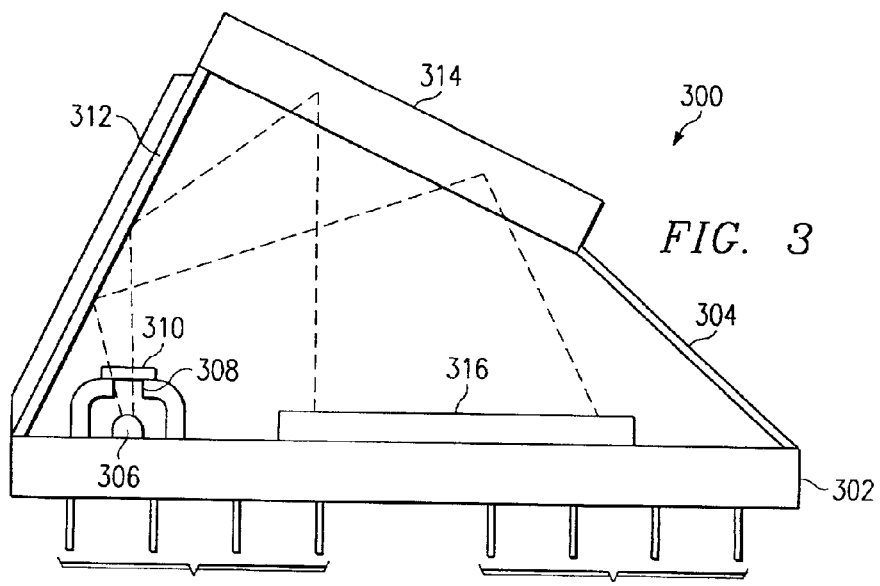
FIG. 3 illustrates an alternate embodiment of an integrally formed surface plasmon resonance sensor.

FIG. 3 illustrates an alternative configuration of an integrally formed SPR 300. This alternative configuration includes a substrate 302 on which the sensor is constructed and on which a light transmissive housing 304 is coupled. A light source 306 is preferably located above or within the substrate 302. Disposed above the light source 306 is a physical aperture 308 through which light from the source 306 passes.

In operation, a polarizer 310 is located near the aperture 308 to polarize the light passing through aperture 308. The polarized light continues through the housing 304 and strikes a thin surface plasmon resonance layer 312. The polarized light is reflected internally from layer 312 and continues through housing 304 and strikes a planar mirror 314. The polarized light reflects from the mirror 314 and is directed through the housing 304 and onto a detector array 316.

As shown in FIG. 3, the light source 306, aperture 308, polarizer 310 and detector array 316 are disposed within housing 304. As with the housing 204 described in FIG. 2, the housing 304 is made of a material that is transparent or substantially transparent to the light from light source 306.

Housing 304 is formed in a geometric configuration so that light from the source 306 will reflect from the SPR layer 312, the mirror 314 and strike detector array 316. Any configuration accomplishing this is suitable, however, there are several considerations that need to be taken into account in designing sensors of the type illustrated in FIGS. 2 and 3. It is desirable to have the radiation impinging on the detector array at angles as close as possible to 90 degrees. This is due to the fact that the sensitivity of the discrete detector elements used in the detector array are most sensitive to light impinging along its optical axis. Light impinging from angles where the light rays are not parallel to the optical axis results in a lower output signal which may be preferred in some embodiments. By designing the structures of FIGS. 2 and 3 to have the light strike the detector array at an angle close to 90 degrees, a detector will have the maximum possible sensitivity. For most purposes, however, if the angle at which light strikes the detector array is between about 60 and 90 degrees, the "off-axis" falloff of each detector in the array is not considered to be a major problem. Indeed, with calibration, the sensor of this invention may use light incidence angles of less than about 45 degrees and still be useful.

It is to be further noted from FIGS. 2 and 3 that the surface plasmon resonance layer may be formed on a surface of the exterior of the housing. It is also possible to have the surface plasmon resonance layer (a thin conductive film) disposed on a glass slide, or the like, which is located adjacent an exterior surface of the housing and having an index matching fluid disposed between the slide and the housing. The mirror may even be formed on an exterior surface of the housing. This mirror will have sufficient mass so that the effect of surface plasmon resonance will not occur on the surface thereof.

Those of skill in the art will recognize that the elements of the integrally formed surface plasmon resonance sensors devices such as those depicted in FIGS. 2 and 3 may be relocated, rearranged or reoriented within the transparent housing while retaining equivalence in function according to the present invention. Further alternative designs are possible. For example, it is possible to use a surface plasmon resonance layer disposed on a curved or featured exterior surface of the housing (not illustrated). Likewise, the mirror may be constructed on a curved surface. It is also possible to have more than one mirror and/or SPR surface disposed along the light path between the source and the detector array. It will also be clear that the light from the source may strike a mirror or a lens prior to striking the surface plasmon resonance layer. Further variations in the radiation path and corresponding structure of the housing may be conceived while retaining the functionality of the sensor illustrated herein.

The structures as illustrated in FIGS. 2 and 3 do not depict filters disposed within the housing. A filter may be disposed between the detector array and the mirror. For example, the filter may be placed adjacent the detector array. Alternatively, the housing may be made of a material transparent to radiation at the frequencies produced by the source and opaque to other frequencies. In either configuration, radiation at frequencies other than those produced by the source will not form a significant portion of the output of the detector array.

The integrally formed sensors may additionally include a temperature sensor disposed adjacent to the surface plasmon resonance (SPR) layer and/or the surface of the housing. The temperature sensor produces an electrical signal indicative of the temperature of the SPR layer during operation thereof. The temperature signal may be used to compensate for apparent changes in the measured index of refraction by the invention as a result of changes in the operating temperature of the device.

The integrally formed sensors may additionally include a reference detector disposed proximately to the light source. Such detector may be used to calibrate the invention over long periods of time since the intensity of a source may vary over time.

The following example of one embodiment of the interaction regulated SPR apparatus and method is included for the sake of completeness of disclosure and to illustrate one of may applications contemplated for the claimed technology.

EXAMPLE

TNT E-Field Assay

Disposable gold-coated glass slides are used as the surface plasmon resonance (SPR)-active surfaces. Other surfaces and coatings known to be compatible with SPR may be alternatively employed. The slides are prepared by depositing 2 nanometers of chromium and 50 nanometers of gold (Au) onto 0.008-inch thick borosilicate glass (Erie Scientific, Erie, Pa.) cut to fit over the sensor surface. Both metal films are deposited by thermal evaporation (Varian model 3118, base pressure less than $2 \times 10^{-7}$ Torr). The gold deposition rate is 0.8–1.0 nanometers/sec, and the chromium deposition rate is 0.1–0.2 nanometers/sec.

Gold-coated slides are stored in Fluoroware boxes in an uncontrolled laboratory ambient. Prior to the attachment of bio-films, the gold SPR surfaces may be routinely cleaned to enhance assay reproducibility. Disposable slides are cleaned with 0.1% Triton X-100 (a non-ionic detergent) and 0.12 N sodium hydroxide (NaOH). Slides are rinsed thoroughly with de-ionized water and dried with nitrogen.

A tri-nitrotoluene (TNT) sensing bio-film is prepared on the disposable gold slides by spreading 0.5 microliters of tri-nitrobenzene bovine serum albumin ("TNB-BSA"—20 micrograms/milliliter in phosphate buffered saline pH 7.4) across the surface of a cleaned gold-coated glass slide using a pipette tip. The slide is allowed to air dry and then placed into a 70° C. vacuum oven for 20 minutes. The TNB-BSA covered slide is rinsed in distilled or purified water and allowed to air dry before assembly on a SPREETA-type SPR sensor(Texas Instruments, Dallas, Tex.).

A flow cell 100 is used in these experiments to enable relatively small fluid volumes to be brought to and from the active portion of the SPR sensing surface. The body of the flow cell 100 used is a ¼-inch thick TEFLON block 114 with holes drilled to accept ¹⁄₁₆-inch OD TFLON tubing. The flow cell 100 is outfitted with a small glass bead thermistor 106. A silicon gasket 112, with a laser-cut channel is placed between the TEFLON block 114 and sensor surface 116. The thermistor 106 may reside directly in the flow cell channel 102. The channel 1–2 is positioned so that it overlaps the active SPR region 116.

The flow cell 100 is assembled and mounted above the TNB-BSA slide. In the E-field assisted assay, the flow cell 100 is modified by the addition of two platinum electrodes 118, 120 in accordance with one embodiment of the present invention. A capacitor is created within the flow cell device 100 by attaching a platinum electrode 118 to the surface of the gold sensing layer 116 and positioning a second platinum electrode 120 above the flow cell channel 102. The liquids and biological buffers used for most biosensing assays serve as the dielectric. The electrodes are constructed using 0.003" thick platinum foil (Electronic Space Products International, Ashland, Oreg.). The first electrode 118 includes a tin strip of platinum placed o top of the gold slide 116 and underneath the silicone gasket 112. The second electrode 120 is a sheet of platinum placed between the silicone gasket 112 and the TEFLON block 114. Three holes are drilled in the sheet of platinum to accommodate the TEFLON tubing 104, 122 and the bead thermistor 106. The two electrodes 118, 120 are generally long enough to protrude from the flow cell 100. After assembly of the flow cell 100, the first electrode 118 protrudes from the top of the sensor 116, while the second electrode 120 protrudes from the bottom of the sensor 116.

The electrodes are connected to a Keithley model 236 source measuring unit ("SMU") (Keithley Instruments Incorporated, Cleveland, Ohio) using a triaxial cable (Model 237-ALG-2, Keithley Instruments Incorporated). The SMU is used to source voltage and measure current during the course of the assay.

After assembling the SPREETA™ type sensor and flow cell, the sensor is air initialized. Liquids may be applied to the sensor surface using a simple peristaltic pump (Fisher brand Variable Flow Peristaltic Pump) operating around 300 microliters/min. An SPR curve is obtained in water. The baseline and other analysis parameters are set using this sample curve.

The sensing surface is then washed with 0.1% Triton X-100 and 0.12 N NaOH to remove any loosely bound TNB-BSA or surface contaminants from the surface of the slide. Following the washing procedure, a baseline is again obtained in 50 mM glycine+0.1% Triton X-100.

Figure 4:
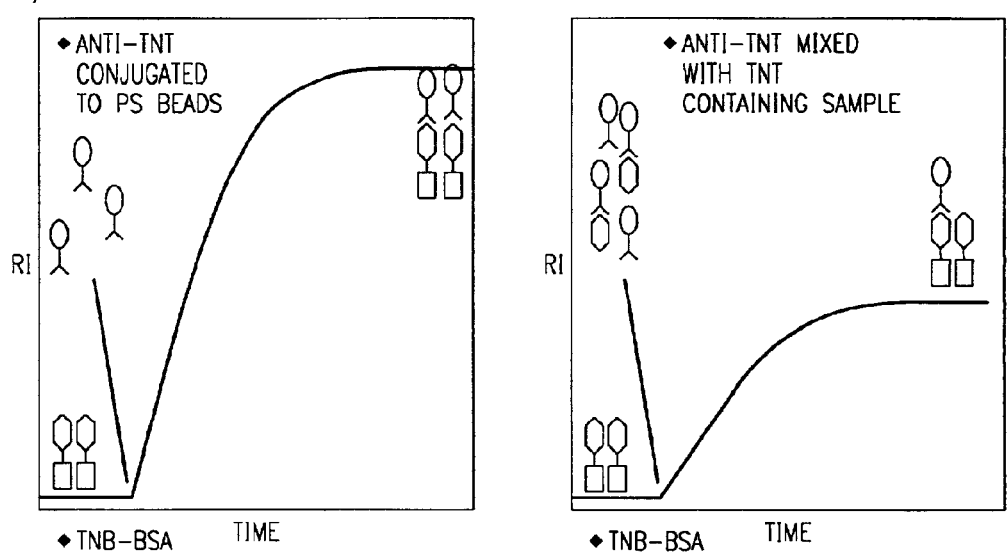
FIG. 4 illustrates one embodiment of a competition assay format in accordance with the present invention.
Figure 5:
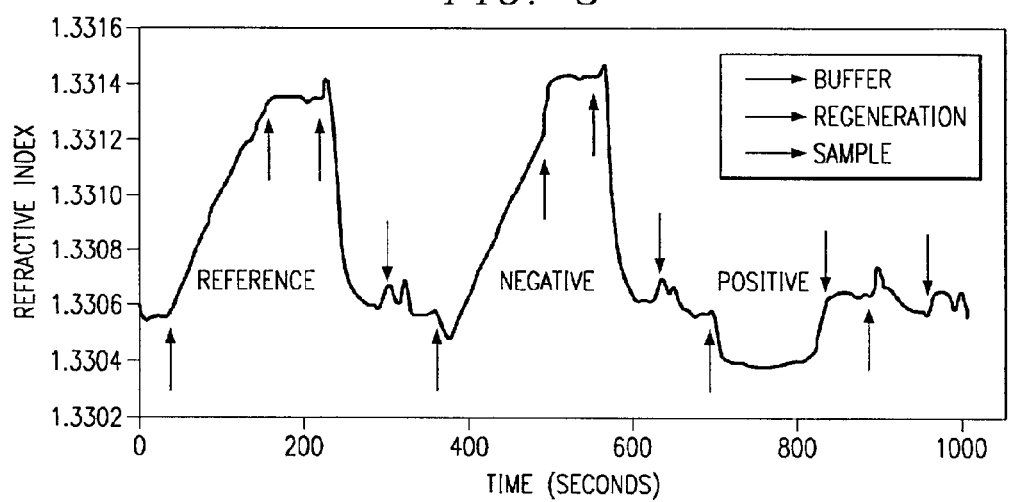
FIG. 5 shows a representative SPR competitive assay refractive index scan obtained in accordance with one embodiment of the present invention.

In a direct binding SPR assay, the analyte is typically bound to an immobilized ligand on the SPR surface. A high level summary of a competition assay format for the TNT assay according to one embodiment of the present invention is illustrated in FIG. 4. In the competition assay, a dilute solution of a monoclonal antibody to TNT is flowed across the sensor surface. The antibody is used as a large mass molecule whose binding is competitively prevented by free TNT in solution. When the antibody binds to the TNB-BSA groups on the gold surface, a linear increase in refractive index is observed. Samples of antibody containing TNT cause a change in the rate of antibody adsorption and in the amount of antibody bound.

In an E-field competition assay, the antibody is conjugated to a negatively charged polystyrene bead. The bead amplifies the changes in refractive index that occur upon binding of the antibody to the sensor surface as a result of its large mass. In addition, negatively charged sulfate groups on the polystyrene bead cause an increase in the rate at which the antibody binds to the TNB-BSA on the sensor surface when a positive bias is applied to the surface. The electric field in the E-field assisted assay helps to transport and concentrate the antibody over its immobilized binding partner and consequently enhances the rate of binding.

To calibrate the SPREETA sensor, 1 ml of anti-TNT antibody conjugated to 0.5 micron diameter beads in 50 mM glycine+0.1% Triton X-100 is introduced within the flow cell. A positive bias is applied to the gold ("Au") surface containing the immobilized TNB-BSA. A typical bias of 1–10 volts pulsed for 1–10 seconds is used. The electric field is subsequently reversed to repulse the non-specific binding of molecules whose affinity for the TNB-BSA is less than that of the anti-TNT antibodies. A typical bias of 1–10 volts per pulse of 1–10 seconds is used. A baseline is obtained in 50 mM glycine+0.1% Triton X-100. Binding of anti-TNT antibody to the sensor surface is measured as a refractive index increase. The peak height for this "reference sample" ([TNT]=0) describes the maximum amount of anti-TNT antibody expected to bind without interference. A reference sample is run periodically to verify that the regeneration process does not affect the ability of the TNB-BSA surface to bind anti-TNT antibody.

The antibody is stripped from the sensor and the surface regenerated using 0.1% Triton+0.12 N NaOH. Antibody binding is examined in the presence of a liquid sample containing either 0 or 1 parts-per-million ("ppm") TNT. The presence of TNT in the liquid sample reduces the amount of antibody binding to the sensor surface. In the example shown on FIG. 5, samples are considered positive for TNT when the amount of antibody binding in the presence of the liquid sample is less than 54% of that obtained when antibody is bound in 50 mM glycine+0.1% Triton X-100 alone.

In contrast, in the TNT assay with the E-field, the same initial steps as above are conducted using antibodies conjugated with negatively charged beads. Beaded antibodies are combined with a liquid sample (that may or may not contain TNT) and the solution is exposed to the sensor surface. A positive bias is placed on the sensor surface (relative to a parallel plate counter electrode) and the bias draws the beaded antibodies immediately toward the surface, resulting in an instantaneously high concentration of antibody at the surface. Reactions are then able to take place in a concentrated local environment. The bias is removed and the beads move away from the surface and only those beads bound by their linked antibodies are expected to remain. After the bias is removed, buffer is again introduced for a new baseline and the difference between the new and old baselines reports the presence and quantity of TNT in the solution. Furthermore, the charged beads not only bring the antibody down to the surface quickly and in high concentration, but they also amplify the SPR signal on a molecule by molecule basis because they increase the size of the specifically bound molecule, thus, amplifying the effect on the surface plasmon resonance. In this example, bead derivatized antibodies are approximately 1 micron in diameter as opposed to the approximately 50 angstrom individual protein.

While this invention has been described with reference to illustrative embodiments, this description is not intended to be construed in a limiting sense. Upon reference to the description, it will be apparent to persons skilled in the art that various modifications and combinations of the illustrative embodiments as well as other embodiments of the invention can be made without departing from the spirit and scope of the invention. It is therefore intended that the appended claims encompass any such modifications or embodiments.

What is claimed is:

1. A sample delivery and sensing unit for directed molecular interaction during surface plasmon resonance analysis comprising:

an electrically conductive surface plasmon resonance layer;

an integrally formed surface plasmon resonance sensor in optic communication with the surface plasmon resonance layer, said sensor having a housing transparent to a given frequency of light, and, within said housing, a source of the given frequency of light directed onto said surface plasmon resonance layer and a photodetector array for receiving said given frequency of light reflected from said plasmon resonance detector; and a flow cell attached to the surface plasmon resonance layer, having a fluid path, said fluid path having an analyte detection chamber disposed along the fluid path, said analyte detection chamber having an interior region in fluidic communication with the surface plasmon resonance layer and having means for generation of a molecular interaction bias across the analyte detection chamber;

wherein the molecular interaction bias is magnetic.

2. A sample delivery and sensing unit for directed molecular interaction during surface plasmon resonance analysis comprising:

an integrally formed surface plasmon sensor having a housing transparent to electromagnetic radiation of a given frequency range and, within said housing, a source of electromagnetic radiation having the given frequency range and a photodetector array disposed adjacent the surface of the housing, such that radiation from the source reflects off the surface and strikes the photodetector array;

a thin surface plasmon resonance layer in optic communication with an exterior surface of the integrally formed surface plasmon resonance sensor; and a fluid path having an analyte detection chamber in fluidic communication with the surface plasmon resonance layer having means for generating a molecular interaction bias across the analyte detection chamber to direct bias responsive conjugated molecules to the surface plasmon resonance layer.

3. The unit of claim 2 wherein the molecular interaction bias is electrical.

4. A sample delivery and sensing unit for directed molecular interaction during surface plasmon resonance analysis comprising:

an integrally formed surface plasmon resonance sensor having a housing transparent to electromagnetic radiation of a given frequency range and, within said housing, a source of electromagnetic radiation having the given frequency range and a photodetector array disposed adjacent the surface of the housing, such that radiation from the source reflects off the surface and strikes the photodetector array;

a thin surface plasmon resonance layer in optic communication with an exterior surface of the integrally formed surface plasmon resonance sensor; and an analyte detection chamber in fluidic communication with the surface plasmon resonance layer having means for generating a molecular interaction bias across the analyte detection chamber to direct bias responsive conjugated molecules to the surface plasmon resonance layer;

wherein the molecular interaction bias is magnetic.

5. A method for kinetically controlled surface plasmon resonance analysis comprising:

providing a surface plasmon resonance sensor having a surface plasmon layer in optical communication with the sensor;

derivatizing the surface plasmon layer;

providing a fluid path having an analyte detection chamber in fluidic communication with the derivatized surface plasmon layer;

providing means in the chamber for generating a molecular interaction bias across the chamber;

providing a conjugate between an analyte and a bias responsive moiety, wherein the analyte is reactive with the derivatized surface plasmon layer and the bias responsive moiety changes the response of the analyte to the molecular interaction bias;

introducing the conjugated analyte into the chamber;

generating the molecular interaction bias within the chamber; and determining changes in surface plasmon resonance due to association of the conjugated analyte to the derivatized surface plasmon layer.

6. The method of claim 5 wherein the molecular interaction bias is electrical.

7. A method for kinetically controlled surface plasmon resonance analysis comprising:

providing a surface plasmon resonance sensor having a surface plasmon layer in optical communication with the sensor;

derivatizing the surface plasmon layer;

placing an analyte detection chamber in fluidic communication with the derivatized surface plasmon layer;

providing means in the chamber for generating a molecular interaction bias across the chamber;

providing a conjugate between an analyte and a bias responsible moiety, wherein the analyte is reactive with the derivatized surface plasmon layer and the bias responsive moiety changes the response of the analyte to the molecular interaction bias;

introducing the conjugated analyte into the chamber;

generating the molecular interaction bias within the chamber; and determining changes in surface plasmon resonance due to association of the conjugated analyte to the derivatized surface plasmon layer;

wherein the molecular interaction bias is magnetic.

8. The method of claim 5 wherein the conjugated analyte is for the kinetically enhanced measurement of molecular interactions in the groups consisting of: avidin-biotin binding, antibody-antigen binding, antibody-antigen dissociation kinetics, protein binding, protein-nucleic acid binding, specific detection of small molecules, concentration of analytes, measurement of oligonucleotide complements, mixture proportions, receptor-ligand interactions, aptamer interactions, and molecular assembly events.

9. The method of claim 8 wherein the conjugated analyte is for the kinetically enhanced measurement of molecular interactions in competitive binding assays.

10. A sample delivery and sensing unit for directed molecular interaction during surface plasmon resonance analysis comprising:

an electrically conductive surface plasmon resonance layer;

an integrally formed surface plasmon resonance sensor in optic communication with the surface plasmon resonance layer, said sensor having a housing transparent to a given frequency of light, and, within said housing, a source of the given frequency of light directed onto said surface plasmon resonance layer and a photodetector array for receiving said given frequency of light reflected from said plasmon resonance detector; and a flow cell attached to the surface plasmon resonance layer, having a fluid path, said fluid path having an analyte detection chamber disposed along the fluid path, said analyte detection chamber having an interior region in fluidic communication with the surface plasmon resonance layer and having means for generation of a molecular interaction bias across the analyte detection chamber.

11. The unit of claim 10 wherein the molecular interaction bias is electrical.

12. The unit of claim 10 wherein said means for generation of a molecular interaction bias across the analyte detection chamber comprises a first electrode coupled to said surface plasmon resonance layer and a second electrode disposed at a surface of said analyte detection chamber opposed to said first electrode.

13. The unit of claim 12 wherein said second electrode forms a part of the fluid path of said analyte detection chamber.

* * * * *